(12) United States Patent
Vrba et al.

(10) Patent No.: US 6,620,114 B2
(45) Date of Patent: Sep. 16, 2003

(54) GUIDEWIRE HAVING A MARKER SEGMENT FOR LENGTH ASSESSMENT

(75) Inventors: Anthony C. Vrba, Maple Grove, MN (US); Peter Skujins, Minneapolis, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/971,410

(22) Filed: Oct. 4, 2001

(65) Prior Publication Data

US 2002/0042582 A1 Apr. 11, 2002

Related U.S. Application Data

(60) Provisional application No. 60/238,184, filed on Oct. 5, 2000.

(51) Int. Cl.[7] .......................... A61B 5/00; A61M 25/00
(52) U.S. Cl. ........................................ 600/585; 33/511
(58) Field of Search ................................ 600/433–435, 600/585, 587; 604/164.13, 529; 33/511, 512

(56) References Cited

U.S. PATENT DOCUMENTS

| | | | |
|---|---|---|---|
| 4,671,291 A | 6/1987 | Wilson | |
| 5,084,022 A | 1/1992 | Claude | |
| 5,253,653 A | * 10/1993 | Daigle et al. | ................ 600/585 |
| 5,345,945 A | * 9/1994 | Hodgson et al. | ............. 600/585 |
| 5,353,808 A | * 10/1994 | Viera | .......................... 600/585 |
| 5,406,960 A | 4/1995 | Corso, Jr. | |
| 5,465,732 A | * 11/1995 | Abele | .......................... 600/585 |
| 5,479,938 A | 1/1996 | Weier | |
| 5,606,981 A | * 3/1997 | Tartacower et al. | ......... 600/585 |
| 5,836,892 A | * 11/1998 | Lorenzo | ...................... 600/585 |
| 5,860,923 A | * 1/1999 | Lenker et al. | ............... 600/433 |
| 6,050,958 A | 4/2000 | Dickinson et al. | |
| 6,179,788 B1 | 1/2001 | Sullivan | |

FOREIGN PATENT DOCUMENTS

| EP | 0 771 572 A1 | 10/1996 |
|---|---|---|
| GB | 2 355 797 A | 10/1999 |

OTHER PUBLICATIONS

Bard, *Floppy with Accumarkers*, Commander Guide Wire Label.
Cordis, *Tip Flexibility Floppy*, ATW Marker Wire label.
Cordis, ATW Marker Wire label.
Cordis, *Tip Flexibility SuperSoft*, Stabilizer Marker Wire label.

* cited by examiner

*Primary Examiner*—Charles A. Marmor, II
(74) *Attorney, Agent, or Firm*—Crompton, Seager & Tufte LLC

(57) ABSTRACT

A guide wire that can be placed in a patient's vasculature or body cavity. The guide wire includes one or more radiopaque markers that can be visualized by fluoroscopy or the like. The markers are preferably spaced apart longitudinally along the guide wire such that the markers and/or spaces between the markers can be used to make measurements of anatomical or artificial structures within the body.

14 Claims, 1 Drawing Sheet

GUIDEWIRE HAVING A MARKER SEGMENT FOR LENGTH ASSESSMENT

This application claims the benefit under 35 U.S.C. §119 of U.S. Provisional Patent Application No. 60/238,184, filed Oct. 5, 2000.

FIELD OF THE INVENTION

The present invention relates to the field of guidewires for percutaneous procedures. The present invention relates particularly to a guidewire having a marker segment.

BACKGROUND OF THE INVENTION

Guidewires are used in a number of procedures within various conduits of the body. In particular, guidewires are used in percutaneous transluminal coronary angioplasty (PTCA) and other coronary procedures. This can involve insertion of the guide wire through an incision in the femoral artery near the groin, advancing the guide wire over the aortic arch, into a coronary artery, and across the lesion to be treated. Guidewires can be inserted directly into the vasculature or within a guide catheter. The distal end of the guidewire ultimately lies directly within the vasculature.

Once the distal end of the guidewire is positioned in the vasculature, devices including catheters can be advanced into position over the guidewire and withdrawn over the guidewire. In various procedures, the length of the device, or length of a portion of the device advanced over the guidewire can be important. For example, if the guidewire is being used for angioplasty, the length of the dilatation balloon is preferably sufficiently long to dilate a coronary lesion without repositioning the angioplasty catheter or exchanging the catheter for a second angioplasty catheter. The placement of a stent often follows angioplasty. When selecting a stent for placement following angioplasty, the length of the stent is preferably sufficient to support the length of the lesion.

What is desired and has not been provided is a guidewire that can be used to easily estimate the length of anatomic or artificial structures percutaneously. Further, what is desired is a guidewire having one or more easily viewable markers with predetermined distance between each marker so that the conjunction of markers provides a scale to a position that a physician can easily and accurately determine distances within a blood vessel.

SUMMARY OF THE INVENTION

The present invention pertains to a guide wire which can be placed in a patient's vasculature or body cavity. The guide wire includes one or more radiopaque markers which can be visualized by fluoroscopy or the like. The markers are preferably spaced apart longitudinally along the guide wire such that the markers and/or spaces between the markers can be used to make measurements of anatomical or artificial structures within the body.

DETAILED DESCRIPTION OF THE INVENTION

Figure 1:
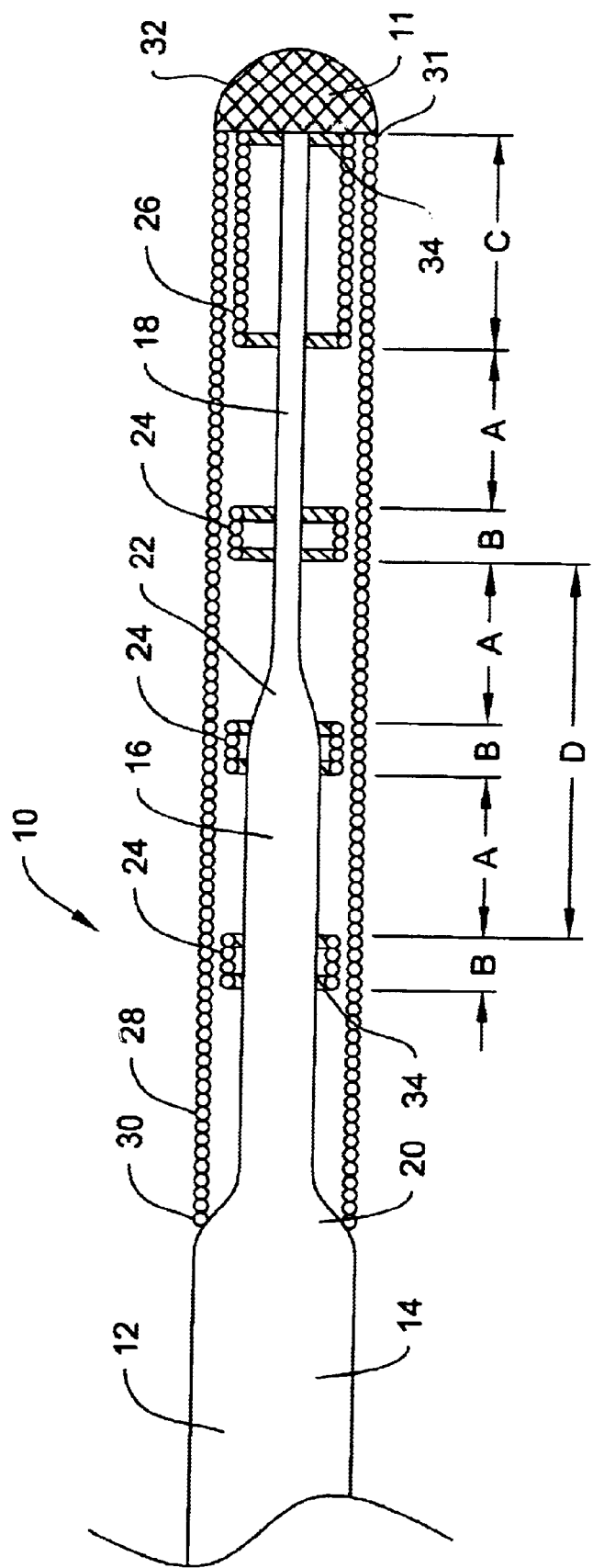
FIG. 1 is a cross-sectional view of a guide wire in accordance with the present invention.

Preferred embodiments of the present invention will be described in detail with reference to the drawings, wherein like reference numerals represent like parts and assemblies throughout the several views. This description does not limit the scope of the invention, which is limited only by the scope of the attached claims.

In general terms, the present invention relates to a guide wire which can be placed in a patient's vasculature or body cavity, wherein the guide wire includes one or more radiopaque markers that are preferably spaced apart longitudinally along the guide wire such that the markers and/or spaces between the markers can be used to make measurements of anatomical or artificial structures within the body.

FIG. 1 is a schematic, cross-sectional view of a guide wire 10 in accordance with the present invention. Guide wire 10 includes a core wire 12 having a proximal end and a distal end 11, the former not being shown. Guide wire 10 preferably includes an elongate core member wire 12. Core wire 12 may be formed in diameters and lengths appropriate to the various percutaneous procedures conducted using guide wires. Core wire 12 may include a proximal first diameter section 14, a more distal, lesser diameter second section 16 and a yet more distal, and lesser diameter third section 18. In a preferred embodiment, core wire 12 includes a first parabolic shaped transition portion 20 between first diameter section 14 and second section 16, and a second parabolic shaped transition portion 22 between second section 16 and third section 18. It can be appreciated that the tapering and reducing of the diameter of a distal region of core wire 12 can make the distal region of guide wire 10 more flexible to enhance steerability of the guide wire. Various combinations of core wire diameter, or cross-sectional reduction proximate distal end 11 can be made without departing from the scope of the present invention.

A rounded atraumatic tip 32 may be adhered to, soldered to or formed at the third section 18 of core wire 12. Surrounding the third section 18 of core wire 12 is a coil 28. A distal end 31 and a proximal end 30 of the coil 28 may be connected by solder, adhesive, or the like to the core wire 12. In a preferred embodiment, the coil 28 may extend proximally to a point where the thickness of core wire 12 has been transitioned to have a diameter approximately equal to the inside diameter of coil 28.

A plurality of radiopaque members are preferably located proximal the distal end 11, including, for example, markers 24 and distal member 26. Markers 24 can be connected to core wire 12 by solder 34, adhesive or the like, including, for example, UV adhesive or TFE (tetrafluoroethylene) tubing.

Core wire 12 and coil 28 are preferably formed from materials less radiopaque than markers 24 and distal member 26. Core wire 12 and coil 28 can be formed from, for example, stainless steel, Nitinol, Inconel®, or other biocompatible materials known to those skilled in the art. Markers 24 and distal member 26 are preferably formed from substantially radiopaque material such as platinum, gold or other substantially radiopaque material. It should be understood, however, that the materials recited herein are merely exemplary and one skilled in the art would know that alternative bio-compatible materials could be advantageously used.

Markers 24 and distal member 26 may be disposed around core member 12. An outer coil 28 can be disposed around core wire 12 and markers 24 and distal member 26. Preferably, markers 24 and distal member 26 may be made of a wire coil that extends around the entire outer circumference of the core member 12. It should be understood that markers 24 and distal member 26 may be formed of a marker band that extends around the entire outer circumference of the core member 12, and the marker coil and/or marker band may be shaped in a variety of shapes, and may extend only partially around the core member 12.

Markers 24 are preferably spaced a distance A from each other and/or distal member 26. Markers 24 preferably have a length B. Although spacing distances A are shown in FIG. 1 as having equal lengths, this equal spacing distance is not required for all embodiments of the present invention. Additionally, although lengths B of marker bands 24 are also shown as being equal, this is also not required for every embodiment of the present invention. Distal member 26 preferably has a length C. The length C of distal member 26 is preferably equal to the sum of spacing distance A and the length B of a single marker 24. Additionally, although length C of distal member 26 is shown as being equal to the sum of spacing distance A and the length B of a single marker 24, this is not required for every embodiment of the present invention.

In a preferred embodiment, spacing distance A is a positive multiple X of marker length B, wherein the positive multiple X is not more than three. For example, spacing distance A could be 15 mm where length B is 5 mm, and wherein the positive multiple X is three. In yet another embodiment, spacing distance A could be 6 mm where length B is 3 mm, wherein the positive multiple X is two. It can be appreciated that numerous spacings A can be selected as positive multiples of three or less of length B. It again should be understood that although in a preferred embodiment, each spacing distance A is equivalent and each marker length B is equivalent as shown, for example, FIG. 1, this arrangement need not be made in accordance with every embodiment of the present invention.

In use as one embodiment of the invention, if spacing distance A were 6 mm and length B were 3 mm, the length of an anatomical or artificial structure could be measured within the body and be estimated within 3 mm. A structure of 3 mm or less will not be longer than the 3 mm length marker B, which under fluoroscopy will appear as a bright mark. A structure 6 mm long will appear when compared to 6 mm spacing distance A, as substantially equivalent in length. It will be appreciated that the space will appear dark under fluoroscopy if a series of 6 mm spacing distances A, are created between a series of 3 mm marker lengths B, and additional length measurements can be made. The length of a structure greater than 6 mm long, but less than 9 mm long, for example, may be estimated by comparing the structure length to the 3 mm length B and an adjacent 6 mm spacing distance A. The length of a structure greater than 9 mm, but less than 12 mm long can be estimated by a comparison to the length B of two 3 mm markers and the 6 mm spacing distance A therebetween. It can be appreciated that additional length measurements can be made at 3 mm increments by comparing additional combinations of 3 mm marker lengths B and 6 mm spacing distances A to a structure. It can be appreciated that although a 3 mm length B and 6 mm spacing distance A has been used for this example, other marker lengths and spacing distances can also be used in accordance with the present invention.

In use as a preferred embodiment of the invention, if spacing distance A were 15 mm and length B were 5 mm, the length of an anatomical or artificial structure could be measured within the body and be estimated within 5 mm. A structure of 15 mm or less will not be longer than the 5 mm length marker, which under fluoroscopy will appear as a bright mark. A structure 15 mm long will appear when compared to 15 mm spacing distance A, as substantially equivalent in length. It will be appreciated that the space will appear dark under fluoroscopy if a series of 15 mm spacing distances A, are created between a series of 5 mm marker lengths B, and additional length measurements can be made. The length of a structure greater than 15 mm long, but less than 20 mm long, for example, may be estimated by comparing the structure length to the 5 mm length B and an adjacent 15 mm spacing distance A. The length of a structure greater than 20 mm, but less than 25 mm long can be estimated by a comparison to the length B of two 5 mm markers and the 15 mm spacing distance A therebetween. It can be appreciated that although a 5 mm length B and 15 mm spacing distance A has been used for this example, other marker lengths and spacing distances can also be used in accordance with the present invention.

As shown in FIG. 1, guide wire 10 includes three spacings A, three markers 24 and a distal member 26. The third marker 24 is disposed along the core wire. In a preferred embodiment, the third marker 24 has a third length that may be equal to the first and second markers 24. The third marker 24 may be spaced from the first member by a second spacing distance, D. The second spacing distance D, may be a positive multiple of the marker length B. It can be appreciated that second spacing distance D may have other spatial relations to the marker length B and spacing distance A. Further, it can be appreciated that fewer or more markers 24 and spacings A can be used in accordance with the present invention.

In a preferred embodiment, spacing distance D is a positive multiple X of marker length B. For example, spacing distance D could be 35 mm where length B is 5 mm, and wherein the positive multiple X is seven. In yet another embodiment, spacing distance D could be 12 mm where length B is 3 mm, wherein the positive multiple X is four. It can be appreciated that numerous spacings D can be selected as positive multiples of length B. It again should be understood that although in a preferred embodiment, each spacing distance D is a positive multiple marker length B as shown, for example, FIG. 1, this arrangement need not be made in accordance with every embodiment of the present invention.

The foregoing description of the invention has been presented for purposes of illustration and description, and is not intended to be exhaustive or to limit the invention to the precise form disclosed. The description was selected to explain the principles of the invention in various embodiments and various modifications as are suited to the particular use contemplated. It is intended that the scope of the invention not be limited by the specification, but defined by the claims set forth below:

What is claimed is:

1. A guidewire, comprising:
   an elongate core wire;
   a distal radiopaque member having a distal length;
   a first radiopaque member having a first length; and
   a second radiopaque member having a second length;
   wherein the distal radiopaque member and the first radiopaque member are longitudinally spaced along the core wire at a first spacing distance and the first radiopaque member and the second radiopaque member are longitudinally spaced along the core wire at the first spacing distance, wherein the first spacing distance is a positive multiple X of the first length, wherein X is not more than three; and
   wherein the distal length is equal to the sum of the first length and the first spacing distance.

2. The guidewire in accordance with claim 1, wherein the first spacing distance is a positive multiple X of the second length, wherein X is not more than three.

3. The guidewire in accordance with claim 2, wherein the first length is equal to the second length.

4. The guidewire in accordance with claim 1, wherein the first radiopaque member includes a coil.

5. The guidewire in accordance with claim 4, wherein the coil is attached to the core wire by a solder joint.

6. The guidewire in accordance with claim 4, wherein the coil includes platinum.

7. The guidewire in accordance with claim 1, wherein the second radiopaque member includes a coil.

8. The guidewire in accordance with claim 7, wherein the coil is attached to the core wire by a solder joint.

9. The guidewire in accordance with claim 7, wherein the coil includes platinum.

10. The guidewire in accordance with claim 1, wherein the distal length is equal to the sum of the first spacing distance and the second length.

11. The guidewire in accordance with claim 1, wherein the distal radiopaque member includes a coil.

12. The guidewire in accordance with claim 11, wherein the coil is attached to the core wire by a solder joint.

13. The guidewire in accordance with claim 11, wherein the coil includes platinum.

14. A method of marking the position of an intravascular feature, the method comprising:

providing a guidewire having a distal radiopaque member, a first radiopaque member and a second radiopaque member disposed along a core wire, the distal radiopaque member having a distal length, the first radiopaque member having a first length and the second radiopaque member having a second length, the distal and first radiopaque members and the first and second members being longitudinally spaced, respectively, along the core wire at a first spacing distance which is a positive multiple X of the first length, wherein X is not more than three, the distal length being the sum of the first length and the first spacing distance;

inserting the guidewire into the vasculature;

positioning the guidewire proximate the intravascular feature; and maintaining the position of the guidewire such that the position of the intravascular feature may be ascertained.

* * * * *